(12) United States Patent
Drahm et al.

(10) Patent No.: US 7,036,355 B2
(45) Date of Patent: *May 2, 2006

(54) VISCOMETER

(75) Inventors: Wolfgang Drahm, Erding (DE); Alfred Rieder, Landshut (DE)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/835,471

(22) Filed: Apr. 30, 2004

(65) Prior Publication Data

US 2004/0200268 A1 Oct. 14, 2004

Related U.S. Application Data

(63) Continuation of application No. 10/226,242, filed on Aug. 23, 2002, now Pat. No. 6,910,366.

(60) Provisional application No. 60/322,743, filed on Sep. 18, 2001.

(30) Foreign Application Priority Data

Aug. 24, 2001 (EP) .................................. 01120343

(51) Int. Cl.
*G01N 11/00* (2006.01)
(52) U.S. Cl. ..................... 73/54.41; 73/54.01
(58) Field of Classification Search .............. 73/54.01, 73/54.41
See application file for complete search history.

(56) References Cited

U.S. PATENT DOCUMENTS

| 4,524,610 A | * | 6/1985 | Fitzgerald et al. ......... 73/54.25 |
| 4,801,897 A | * | 1/1989 | Flecken ....................... 331/65 |
| 5,531,126 A | * | 7/1996 | Drahm .................. 73/861.357 |
| 5,602,345 A | * | 2/1997 | Wenger et al. ......... 73/861.357 |
| 5,661,232 A | * | 8/1997 | Van Cleve et al. ........ 73/54.05 |

* cited by examiner

*Primary Examiner*—Daniel S. Larkin
(74) *Attorney, Agent, or Firm*—Bacon & Thomas

(57) ABSTRACT

The viscometer provides a viscosity value ($X_\eta$) which represents the viscosity of a fluid flowing in a pipe connected thereto. It comprises a vibratory transducer with at least one flow tube for conducting the fluid, which communicates with the pipe. Driven by an excitation assembly, the flow tube is vibrated so that friction forces are produced in the fluid. The viscometer further includes meter electronics which feed an excitation current ($i_{exc}$) into the excitation assembly. By means of the meter electronics, a first internal intermediate value ($X_1$) is formed, which corresponds with the excitation current ($i_{exc}$) and thus represents the friction forces acting in the fluid. According to the invention, a second internal intermediate value ($X_2$), representing inhomogeneities in the fluid, is generated in the meter electronics, which then determine the viscosity value ($X_\eta$) using the two intermediate values ($X_1$, $X_2$). The first internal intermediate value ($X_1$) is preferably normalized by means of an amplitude control signal ($y_{AM}$) for the excitation current ($i_{exc}$), the amplitude control signal corresponding with the vibrations of the flow tube. As a result, the viscosity value ($X_\eta$) provided by the viscometer is highly accurate and robust, particularly independently of the position of installation of the flow tube.

11 Claims, 6 Drawing Sheets

VISCOMETER

CROSS-REFERENCE TO RELATED APPLICATION

This application is a continuation of U.S. application Ser. No. 10/226,242, filed Aug. 23, 2002 now U.S. Pat. No. 6,910,366, and claims the benefit of the filing of Provisional Application No. 60/322,743, filed Sep. 18, 2001.

BACKGROUND OF THE INVENTION

1. Field of the Invention

This invention relates to a viscometer for a fluid flowing in a pipe and to a method of determining the viscosity of the fluid.

2. Discussion of the Prior Art

In measurement and automation technology, the viscosity of a fluid flowing in a pipe, particularly of a liquid, is frequently determined by means of meters which, using a vibratory transducer and meter electronics connected thereto, induce internal friction forces in the fluid and derive therefrom a measurement signal representative of the respective viscosity.

Such viscometers are described, for example, in U.S. Pat. No. 4,524,610 in published International Application WO-A 95/16897 and comprise:
  a vibratory transducer
  with an essentially straight flow tube for conducting the fluid, said flow tube communicating with the pipe and vibrating in operation,
  an excitation assembly for vibrating the flow tube,
  a central axis of the vibrating flow tube being essentially left in its shape and spatial position, so that the flow tube practically does not leave a static rest position assigned to it,
  a sensor arrangement for sensing vibrations of the flow tube and for generating at least one sensor signal representing the vibrations of the flow tube; and
  meter electronics which deliver
  an excitation current for the excitation assembly and
  at least one measured value representing the instantaneous viscosity of the fluid,
  the meter electronics
  adjusting the excitation current by means of the at least one sensor signal and
  generating by means of the excitation current an internal intermediate value representing instantaneous frictions in the fluid, and
  the meter electronics determining the viscosity value using the internal intermediate value.

It has turned out, however, that in spite of viscosity and density being maintained virtually constant, particularly under laboratory conditions, the viscosity value determined by means of the excitation current may exhibit considerable inaccuracies, which may amount to as much as one hundred times the actual viscosity of the fluid.

In U.S. Pat. No. 4,524,610, a possible cause of this problem is indicated, namely the fact that gas bubbles in the fluid may be trapped at the wall of the flow tube. To avoid this problem, it is proposed to install the transducer so that the straight flow tube is in an essentially vertical position, so that the trapping of bubbles is prevented. This, however, is a very specific solution which is only conditionally realizable, particularly in industrial process measurement technology. On the one hand, the pipe into which the transducer is to be inserted would have to be adapted to the latter and not vice versa, which probably cannot be conveyed to the user. On the other hand, the flow tubes may also have a curved shape, so that the problem cannot be solved by adapting the position of installation. It has also turned out that the aforementioned inaccuracies of the measured viscosity value cannot be appreciably reduced even if a vertically installed, straight flow tube is used. Variations in the measured viscosity value of a moving fluid cannot be prevented in this manner, either.

SUMMARY OF THE INVENTION

Therefore, an object of the invention is to provide a viscometer for fluids which, particularly when the fluid is flowing, provides a highly accurate and robust viscosity value essentially independently of, on the one hand, the position of installation of the flow tube and, on the other hand, the vibrations of the flow tube, particularly of their amplitude.

To attain the object, a first variant of the invention provides a viscometer for a fluid flowing in a pipe, said viscometer comprising:
  a vibratory transducer
  at least one flow tube for conducting the fluid and for generating friction forces acting in the fluid, the at least one flow tube communicating with the pipe and vibrating in operation, and
  an excitation assembly for vibrating the at least one flow tube; and meter electronics which deliver
  an excitation current for the excitation assembly and
  a viscosity value representing the instantaneous viscosity of the fluid,
  the meter electronics generating
  a first internal intermediate value, corresponding with the excitation current and representing the friction forces acting in the fluid, and
  a second internal intermediate value, representing inhomogeneities in the fluid, and
  the meter electronics determining the viscosity value using the first and second internal intermediate values.

A second variant of the invention provides a viscometer for a fluid flowing in a pipe, said viscometer comprising:
  a transducer, particularly a flexural mode transducer,
  at least one flow tube for conducting the fluid and for producing friction forces acting in the fluid, the at least one flow tube communicating with the pipe and vibrating in operation,
  an excitation assembly for vibrating the at least one flow tube, and
  a sensor arrangement for sensing vibrations of the flow tube and for generating at least a first sensor signal representing said vibrations; and
  meter electronics which deliver
  an excitation current for the excitation assembly and
  a viscosity value representing the instantaneous viscosity of the fluid,
  the meter electronics
  deriving from the at least first sensor signal an amplitude control signal serving to adjust the excitation current, and
  determining the viscosity value by means of the at least first sensor signal and the amplitude control signal.

Furthermore, the invention provides a method of determining the viscosity of a fluid flowing in a pipe, said method comprising the steps of:
  feeding an excitation current into an excitation assembly mechanically coupled to a flow tube conducting the fluid, for causing mechanical vibrations, particularly flexural vibrations, of the flow tube;

vibrating the flow tube for producing internal friction forces in the fluid;

sensing vibrations of the flow tube for generating a first internal intermediate value, representing friction forces acting in the fluid;

producing a sampling of first internal intermediate values;

using the sampling to determine a second internal intermediate value, representing inhomogeneities in the fluid; and generating a measured viscosity value by means of the two internal intermediate values.

In a first preferred embodiment of the viscometer of the invention, the meter electronics determine the second internal intermediate value by means of the excitation current.

In a second preferred embodiment of the viscometer of the invention, the flow tube for producing friction forces acting in the fluid vibrates at least in part in a flexural mode.

In a third preferred embodiment of the viscometer of the invention, to generate the measured viscosity value, the meter electronics determine by means of the at least first sensor signal a velocity value which represents motions causing the friction forces in the fluid.

In a fourth preferred embodiment of the viscometer of the invention, the meter electronics determine the first internal intermediate value, which corresponds with the excitation current and represents the friction forces acting in the fluid, by means of the amplitude control signal.

In a fifth preferred embodiment of the viscometer of the invention, to generate the viscosity value, the meter electronics normalize the first internal intermediate value to the velocity value.

In a sixth preferred embodiment of the viscometer of the invention, the meter electronics comprise a volatile data memory holding a sampling of first internal intermediate values, and generate the second internal intermediate value by means of the sampling.

In a seventh preferred embodiment of the viscometer of the invention, the second internal intermediate value is generated using a standard deviation of the first internal intermediate value, which is estimated by means of the sampling.

In a first preferred embodiment of the method of the invention, at least one sensor signal representing the vibrations of the flow tube is generated, and the excitation current is adjusted using the at least one sensor signal.

In a second preferred embodiment of the method of the invention, a velocity value which represents a velocity of a motion causing the friction forces acting in the fluid is determined using the sensor signal, and the first internal intermediate value is normalized to the velocity value.

The invention is predicated on recognition that the excitation power fed into the transducer to maintain the vibrations of the flow tube, and thus the viscosity value derived therefrom, may be affected in a disproportionately great measure by inhomogeneities in the fluid, such as gas bubbles or entrained particles of solid matter. The invention is also predicated on recognition that the excitation power can also be determined very precisely in a very simple manner by means of adjustment signals or adjustment values generated within the meter electronics, and that both the adjustment signals for the excitation power and the actually injected excitation power, particularly in the case of flow-tube vibrations with an amplitude regulated at constant value, are too inaccurate by themselves for robust viscosity measurement.

A fundamental idea of the invention is to derive from the excitation power an internal measured value, particularly independently of the type of fluid involved, which represents the inhomogeneities in the fluid relevant to the viscosity measurement and which is a measure of their effect on the measured viscosity value.

Another fundamental idea of the invention is to determine the viscosity value by means of adjustment signals or adjustment values for the excitation power that are generated within the meter electronics, and by means of vibrations of the flow tube that are maintained by the actually injected excitation power. This indirect determination of the excitation power has the advantage of eliminating the need for an additional measurement of the injected excitation power for the purpose of determining the viscosity value.

A further advantage of the invention therefore consists in the fact that it can also be implemented in commercially available Coriolis mass flowmeter-densimeters, for example, and virtually independently of the concrete shape and number of flow tubes used in the respective transducer, i.e., without any basic change in the mechanical design of the transducer.

BRIEF DESCRIPTION OF THE DRAWINGS

The invention and further advantages will become more apparent from the following description of embodiments taken in conjunction with the accompanying drawings, in which like parts are designated by like reference characters throughout the various figures; reference characters that have already been allotted are omitted in subsequent figures if this contributes to clarity. In the drawings.

DESCRIPTION OF THE PREFERRED EMBODIMENTS

Figure 1:
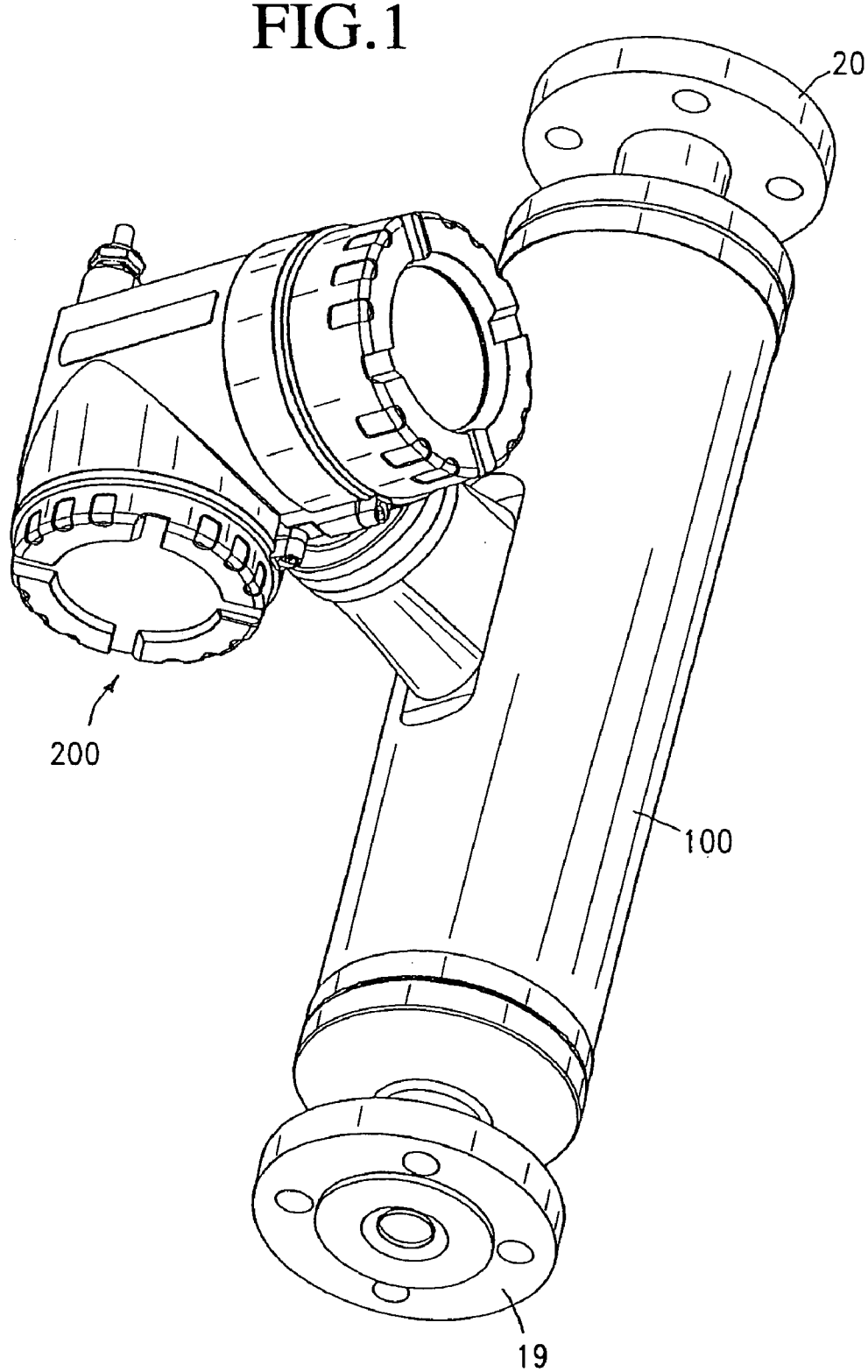
FIG. 1 is a perspective view of a viscometer for generating a viscosity value.
Figure 2:
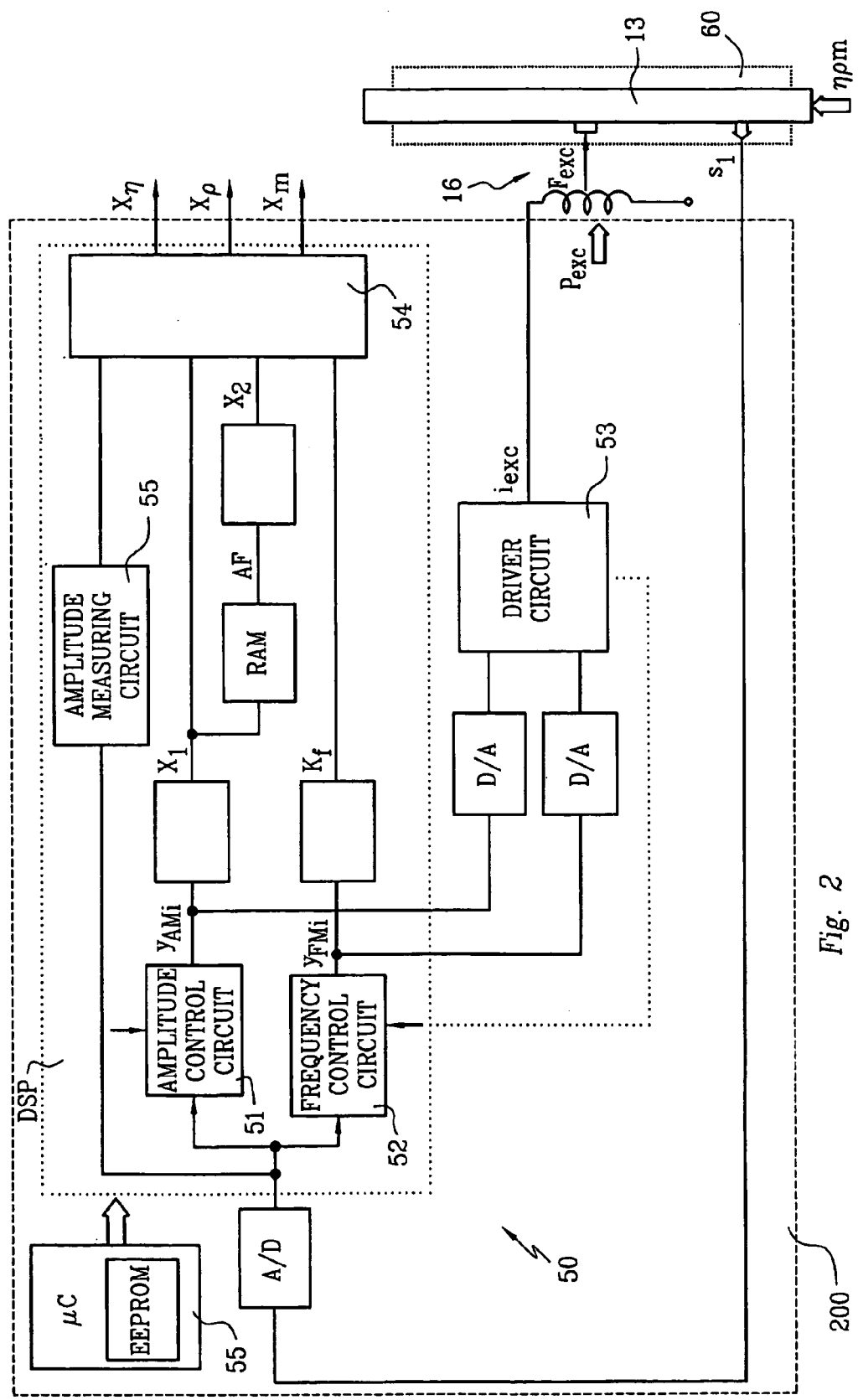
FIG. 2 is a block diagram of a preferred embodiment of meter electronics suitable for the viscometer of FIG. 1.

FIG. 1 shows schematically a viscometer with a vibratory transducer 10, preferably housed in a transducer case 100, and with meter electronics 50, housed in an electronics case 200 and, as shown in FIG. 2, electrically connected to transducer 10. The viscometer serves in particular to sense a viscosity, $\eta$, of a fluid flowing in a pipe (not shown) and to map this viscosity into a measured viscosity value $X_\eta$ representing this viscosity $\eta$. By means of transducer 10, which is driven by meter electronics 50, friction forces are generated in the fluid passing therethrough which are dependent on the viscosity $\eta$ and react on transducer 10 in a measurable manner, i.e., which can be detected using sensor technology and converted into useful input signals for subsequent evaluation electronics.

In the preferred case where the viscometer is designed to be coupled to a field bus, the, preferably programmable, meter electronics 50 will include a suitable communication interface for data communication, e.g., for the transmission of the measurement data to a higher-level stored program control or a higher-level process control system.

Figure 3:
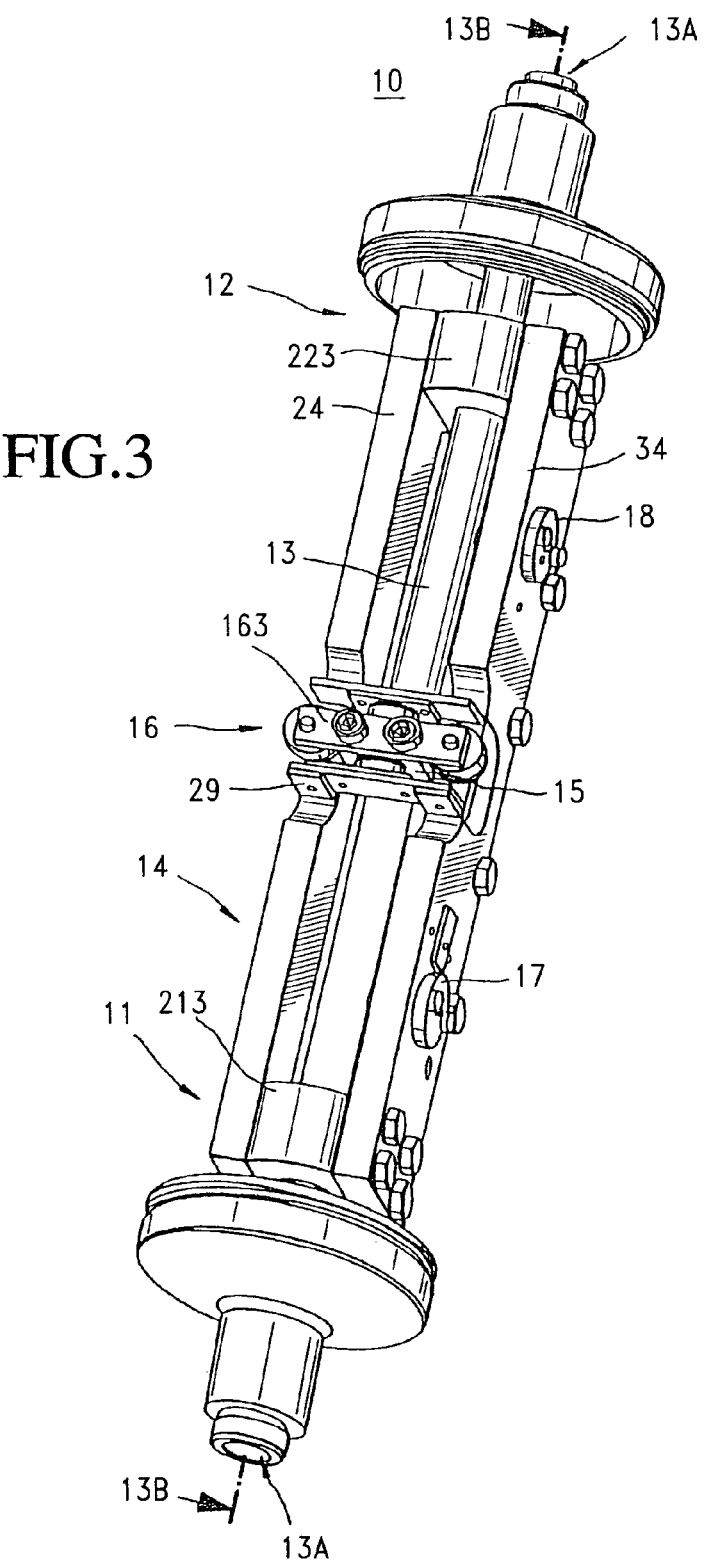
FIG. 3 is a part-sectional, first perspective view of an embodiment of a vibratory transducer suitable for the viscometer of FIG. 1.
Figure 4:
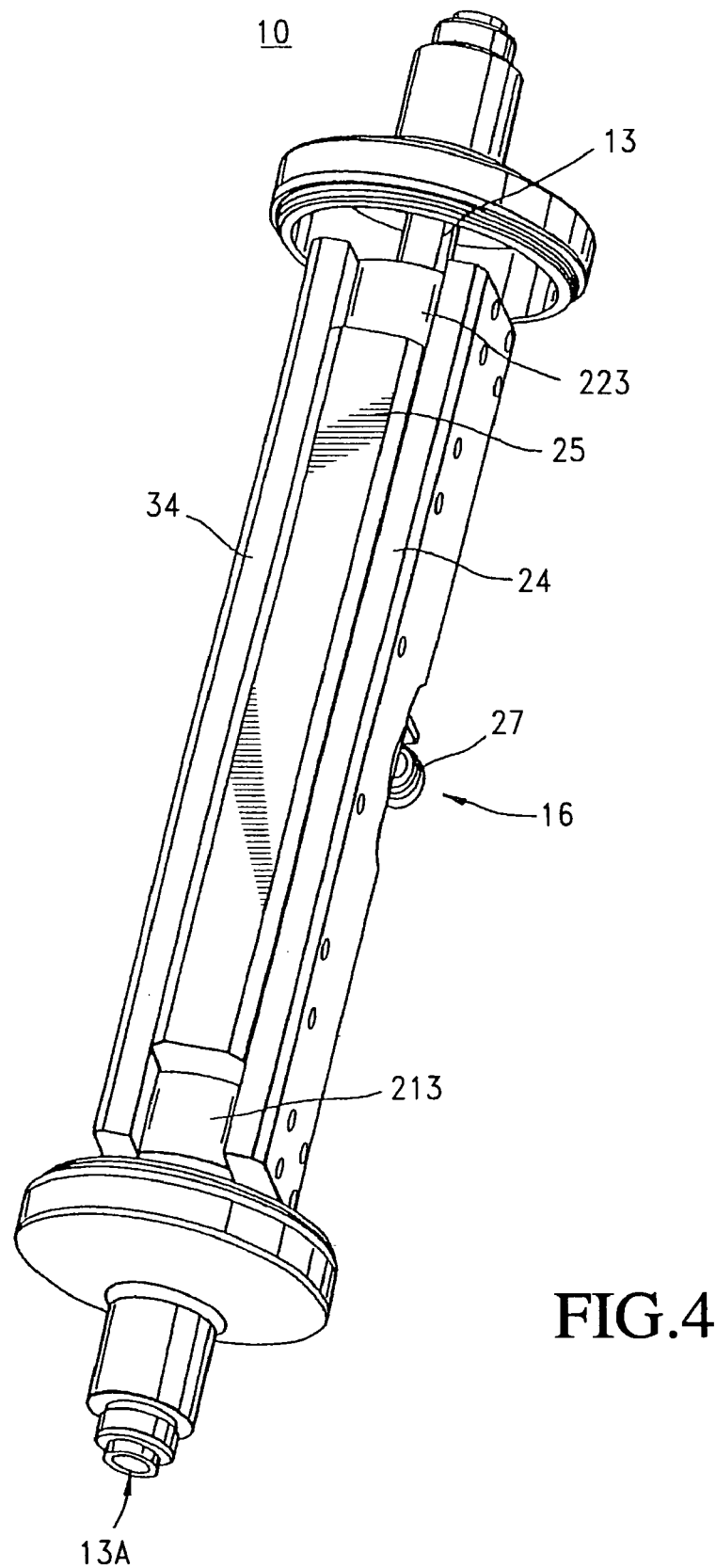
FIG. 4 is a second perspective view of the transducer of FIG. 3.

FIGS. 3 and 4 show an embodiment of a transducer 10 in the form of a physical-to-electrical vibratory transducer assembly. The construction of such a transducer assembly is described in detail in U.S. Pat. No. 6,006,609, for example. Such transducers are already used in commercially available Coriolis mass flowmeter-densimeters as are offered by the applicant with its "PROMASS I" series, for example.

To conduct the fluid to be measured, transducer 10 comprises at least one flow tube 13 of a predeterminable, elastically deformable lumen 13A and a predeterminable nominal diameter, which has an inlet end 11 and an outlet end 12. "Elastic deformation" of lumen 13A as used herein means that in order to produce reaction forces in the fluid, i.e., forces describing the fluid, namely shearing or friction forces, but also Coriolis forces and/or mass inertial forces, in operation, a three-dimensional shape and/or a spatial position of lumen 13A are changed in a predeterminable cyclic manner, particularly periodically, within an elasticity range of flow tube 13; see, for example, U.S. Pat. No. 4,801,897, U.S. Pat. No. 5,648,616, U.S. Pat. No. 5,796,011, and/or U.S. Pat. No. 6,006,609.

At this point is should be noted that instead of a transducer according to the embodiment of FIGS. 3 and 4, virtually any transducer known to the person skilled in the art for Coriolis flowmeter-densimeters, particularly a flexural mode transducer with a bent or straight flow tube vibrating exclusively or at least in part in a flexural mode, can be used for implementing the invention. Further suitable implementations of transducer assemblies that can be used for transducer 10 are described, for example, in U.S. Pat. Nos. 5,301,557, 5,357,811, 5,557,973, 5,602,345, 5,648,616, or 5,796,011, which are incorporated herein by reference.

Materials especially suited for flow tube 13, here an essentially straight tube, are titanium alloys, for example. Instead of titanium alloys, other materials commonly used for such flow tubes, particularly for bent tubes, such as stainless steel or zirconium, may be employed.

Flow tube 13, which communicates at the inlet and outlet ends with the fluid-conducting pipe in the usual manner, is clamped in a rigid support frame 14, particularly in a flexurally and torsionally stiff frame, so as to be capable of vibratory motion, the support frame being preferably enclosed by a transducer case 100.

Support frame 14 is fixed to flow tube 13 by means of an inlet plate 223 at the inlet end and by means of an outlet plate 213 at the outlet end, the two plates being penetrated by respective corresponding extension pieces of flow tube 13. Support frame 14 has a first side plate 24 and a second side plate 34, which are fixed to inlet plate 213 and outlet plate 223 in such a way as to extend essentially parallel to and in spaced relationship from flow tube 13; see FIG. 3. Thus, facing side surfaces of the two side plates 24, 34 are also parallel to each other.

Advantageously, a longitudinal bar 25 serving as a balancing mass for absorbing vibrations of flow tube 13 is secured to side plates 24, 34 in spaced relationship from flow tube 13. As shown in FIG. 4, longitudinal bar 25 extends essentially parallel to the entire oscillable length of flow tube 13; this, however is not mandatory; if necessary, longitudinal bar 25 may also be shorter, of course.

Thus, support frame 14 with the two side plates 24, 34, inlet plate 213, outlet plate 223, and the optional longitudinal bar 25 has a longitudinal axis of gravity which is essentially parallel to a central flow tube axis 13B, which joins inlet end 11 and outlet end 12.

In FIGS. 3 and 4, it is indicated by the heads of the screws shown that the aforementioned fixing of side plates 24, 34 to inlet plate 213, to outlet plate 223 and to longitudinal bar 25 may be done by screwing; it is also possible to use other suitable forms of fastening familiar to those skilled in the art.

If transducer 10 is to be nonpermanently connected with the pipe, flow tube 13 preferably has an inlet-side first flange 19 and an outlet-side second flange 20 formed thereon, see FIG. 1; instead of flanges 19, 20, so-called Triclamp connections, for example, may be used to provide the nonpermanent connection with the pipe, as indicated in FIG. 3.

If necessary, however, flow tube 13 may also be connected with the pipe directly, e.g., by welding or brazing.

To produce the above-mentioned friction forces, during operation of transducer 10, flow tube 13, driven by an electromechanical excitation assembly 16 coupled to the flow tube, is caused to vibrate in the so-called useful mode at a predeterminable frequency, particularly at a natural resonance frequency which is also dependent on a density, ρ, of the fluid, whereby the flow tube is elastically deformed in a predeterminable manner.

In the embodiment shown, the vibrating flow tube 13, as is usual with such flexural mode transducer assemblies, is spatially, particularly laterally, deflected from a static rest position; the same applies to transducer assemblies in which one or more bent flow tubes perform cantilever vibrations about a corresponding longitudinal axis joining the respective inlet and outlet ends, or to those in which one or more straight flow tubes perform only planar flexural vibrations about their longitudinal axis. In the other case where transducer 10 is a radial mode transducer assembly and the vibrating flow tube is symmetrically deformed in the usual manner as is described, for example, in WO-A 95/16897, the flow tube is essentially left in its static rest position.

Excitation assembly 16 serves to produce an excitation force $F_{exc}$ acting on flow tube 13 by converting an electric excitation power $P_{exc}$ supplied from meter electronics 50. The excitation power $P_{exc}$ serves virtually only to compensate the power component lost in the vibrating system because of mechanical and fluid friction. To achieve as high an efficiency as possible, the excitation power $P_{exc}$ is preferably precisely adjusted so that essentially the vibrations of flow tube 13 in the useful mode, e.g., those at a lowest resonance frequency, are maintained.

Figure 5:
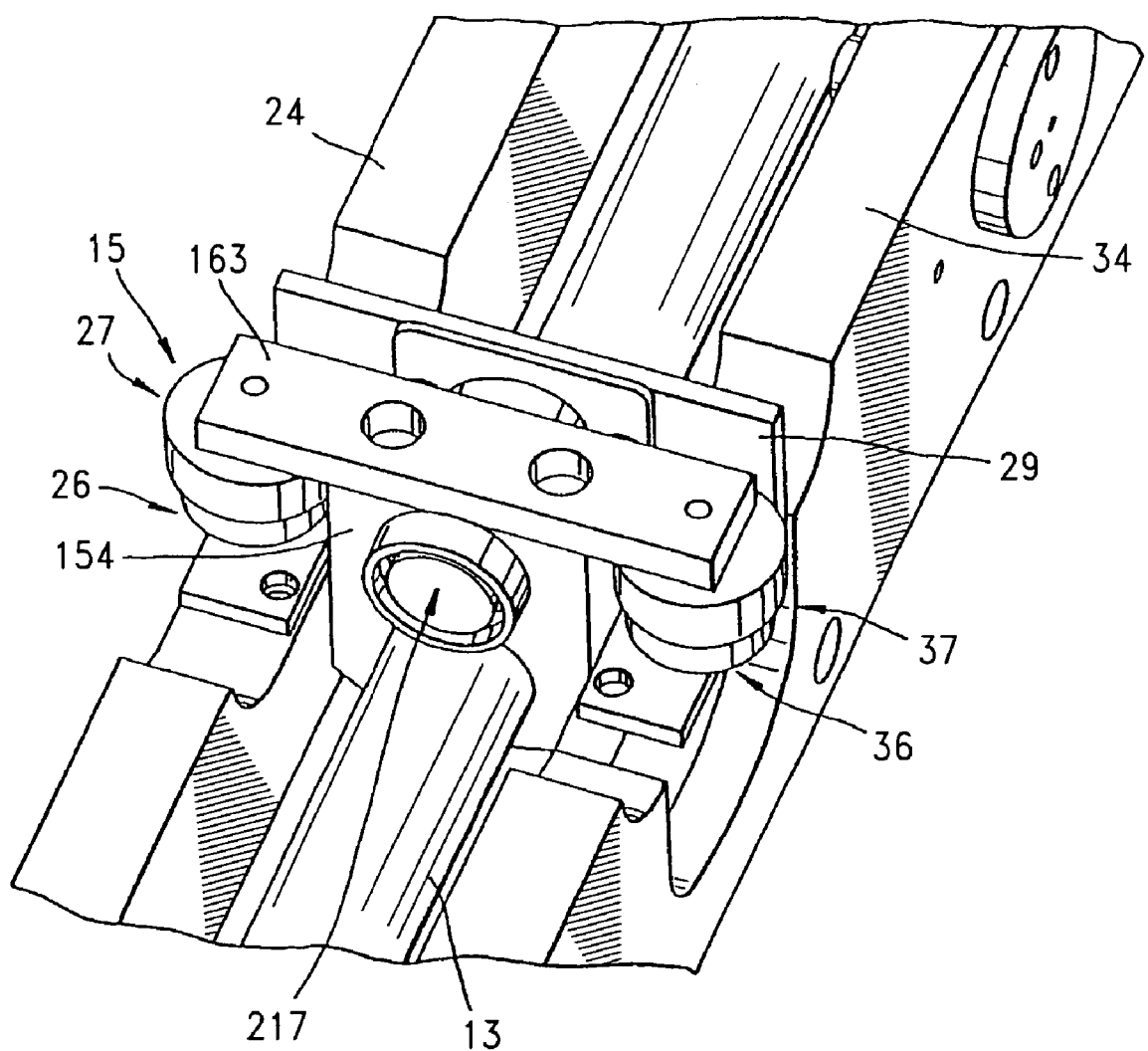
FIG. 5 shows an embodiment of an electromechanical excitation assembly for the transducer of FIG. 3.

For the purpose of transmitting the excitation force $F_{exc}$ to flow tube 13, excitation assembly 16, as shown in FIG. 5, has a rigid, electromagnetically and/or electrodynamically driven lever arrangement 15 with a cantilever 154 and a yoke 163, the cantilever 154 being rigidly fixed to flow tube 13. Yoke 163 is rigidly fixed to an end of cantilever 154 remote from flow tube 13, such that it lies above and extends transversely of flow tube 13. Cantilever 154 may be a metallic disk, for example, which receives flow tube 13 in a bore. For further suitable implementations of lever arrangement 15, reference is made to the above-mentioned U.S. Pat. No. 6,006,609. As is readily apparent from FIG. 2, lever arrangement 15, here a T-shaped arrangement, is preferably arranged to act on flow tube 13 approximately midway between inlet end 11 and outlet end 12, so that in operation, flow tube 13 will exhibit its maximum lateral deflection in the middle.

To drive the lever arrangement 15, excitation assembly 16, as shown in FIG. 5, comprises a first excitation coil 26 and an associated first armature 27 of permanent-magnet material as well as a second excitation coil 36 and an associated second armature 37 of permanent-magnet material. The two excitation coils 26 and 36, which are preferably electrically connected in series, are fixed to support frame 14 on both sides of flow tube 13 below yoke 163, particularly nonpermanently, so as to interact in operation with their associated armatures 27 and 37, respectively. If necessary, the two excitation coils 26, 36 may, of course, be connected in parallel.

As shown in FIGS. 3 and 5, the two armatures 27, 37 are fixed to yoke 163 at such a distance from each other that during operation of transducer 10, armature 27 will be penetrated essentially by a magnetic field of excitation coil 26, while armature 37 will be penetrated essentially by a magnetic field of excitation coil 36, so that the two armatures will be moved by the action of corresponding electrodynamic and/or electromagnetic forces.

The motions of armatures 27, 37 produced by the magnetic fields of excitation coils 26, 36 are transmitted by yoke 163 and cantilever 154 to flow tube 13. These motions of armatures 27, 37 are such that yoke 163 is displaced from its rest position alternately in the direction of side plate 24 and in the direction of side plate 34. A corresponding axis of rotation of lever arrangement 15, which is parallel to the above-mentioned central axis 13B of flow tube 13, may pass through cantilever 154, for example.

Particularly in order to hold excitation coils 26, 36 and individual components of a magnetic brake assembly 217, which is described below, support frame 14 further comprises a holder 29 for electromechanical excitation assembly 16. Holder 29 is connected, preferably nonpermanently, with side plates 24, 34.

In the transducer 10 of the embodiment, the lateral deflections of the vibrating flow tube 13, which is firmly clamped at inlet end 11 and outlet end 12, simultaneously cause an elastic deformation of its lumen 13A; this elastic deformation extends virtually over the entire length of flow tube 13.

Furthermore, due to a torque acting on flow tube 13 via lever arrangement 15, torsion is induced in flow tube 13 about central axis 13B simultaneously with the lateral deflections, at least in sections of the tube, so that the latter vibrates in a mixed flexural and torsional mode serving as a useful mode. The torsion of flow tube 13 may be such that the direction of a lateral displacement of the end of cantilever 154 remote from flow tube 13 is either the same as or opposite to that of the lateral deflection of flow tube 13. In other words, flow tube 13 can perform torsional vibrations in a first flexural and torsional mode, corresponding to the former case, or in a second flexural and torsional mode, corresponding to the latter case. In the transducer 10 according to the embodiment, the natural resonance frequency of the second flexural and torsional mode, e.g., 900 Hz, is approximately twice as high as that of the first flexural and torsional mode.

In the preferred case where flow tube 13 is to perform vibrations only in the second flexural and torsional mode, excitation assembly advantageously incorporates a magnetic brake assembly 217 based on the eddy-current principle, which serves to stabilize the position of the axis of rotation. By means of magnetic brake assembly 217 it can thus be ensured that flow tube 13 always vibrates in the second flexural and torsional mode, so that any external interfering effects on flow tube 13 will not result in a spontaneous change to another flexural and torsional mode, particularly to the first. Details of such a magnetic brake assembly are described in detail in U.S. Pat. No. 6,006,609, for example; furthermore, the use of such magnetic brake assemblies is known from transducers of the aforementioned "PROMASS I" series.

At this point if should be mentioned that in the flow tube 13 deflected in this manner according to the second flexural and torsional mode, the central axis 13B is slightly deformed, so that during the vibrations, this axis spreads a slightly curved surface rather than a plane. Furthermore, a path curve lying in this surface and described by the midpoint of the central axis of the flow tube has the smallest curvature of all path curves described by this central axis.

To detect the deformations of flow tube 13, transducer 10 comprises a sensor arrangement 60 with at least a first sensor 17, which provides a first, preferably analog, sensor signal $s_1$ in response to vibrations of flow tube 13. As is usual with such transducers, sensor 17 may be formed, for example, by an armature of permanent-magnet material fixed to flow tube 13 and interacting with a sensor coil held by support frame 14.

Sensor types especially suited for sensor 17 are those which sense the velocity of the deflections of the flow tube based on the electrodynamic principle. It is also possible to use acceleration-measuring electrodynamic or displacement-measuring resistive or optical sensors, or other sensors familiar to those skilled in the art which are suitable for detecting such vibrations.

In a preferred embodiment of the invention, sensor arrangement 60 further comprises a second sensor 18, particularly a sensor identical to the first sensor 17, which second sensor 18 provides a second sensor signal $s_2$ representing vibrations of the flow tube. In this embodiment, the two sensors 17, 18 are positioned at a given distance from each other along flow tube 13, particularly at the same distance from the middle of flow tube 13, such that sensor arrangement 60 detects both inlet-side and outlet-side vibrations of flow tube 13 and provides corresponding sensor signals $s_1$ and $s_2$, respectively. The first sensor signal $s_1$ and, if present, the second sensor signal $s_2$, which usually each have a frequency corresponding to the instantaneous vibration frequency of flow tube 13, are fed to meter electronics 50, as shown in FIG. 2.

To vibrate the flow tube 13, excitation assembly 16 is supplied from meter electronics 50 with a likewise oscillating, unipolar or bipolar excitation current $i_{exc}$ of adjustable amplitude and adjustable frequency $f_{exc}$, such that in operation, excitation coils 26, 36 are traversed by this current to produce the magnetic field necessary to move armatures 27, 37. Thus, the excitation force $F_{exc}$ required to vibrate flow tube 13 can be monitored and adjusted in amplitude, e.g., by means of a current- and/or voltage-regulator circuit, and in frequency, e.g., by means of a phase-locked loop, in the manner familiar to those skilled in the art. The excitation current $i_{exc}$ delivered by meter electronics 50 is preferably a sinusoidal current, but it may also be a pulsating, triangular, or square-wave alternating current, for example.

As is usual in viscometers of the kind being described, the frequency $f_{exc}$ of the excitation current $i_{exc}$ is equal to the predetermined vibration frequency of flow tube 13, and is therefore preferably set at an instantaneous natural resonance frequency of the fluid-carrying flow tube 13. As indicated above, the invention proposes for the transducer 10 according to the embodiment that the excitation current $i_{exc}$ should be caused to flow through the two excitation coils 26, 36 and that its frequency $f_{exc}$ should be chosen so that the laterally oscillating flow tube 13 is, if possible, twisted exclusively according to the second flexural and torsional mode.

To generate and adjust the excitation current $i_{exc}$, meter electronics 50 comprise a driver circuit 53 which is controlled by a frequency control signal $y_{FM}$, representing the excitation frequency to be adjusted, $f_{exc}$, and by an amplitude control signal $y_{AM}$, representing the amplitude of excitation current $i_{exc}$ to be adjusted. The driver circuit may be implemented with a voltage-controlled oscillator followed by a voltage-to-current converter, for example; instead of an analog oscillator, a numerically controlled digital oscillator, for example, may be used to adjust the excitation current $i_{exc}$.

The amplitude control signal $y_{AM}$ may be generated with an amplitude control circuit 51 incorporated in meter electronics 50, which updates at least one of the two sensor signals $s_1$, $s_2$ and the amplitude control signal $y_{AM}$ based on the instantaneous amplitude and on a constant or variable amplitude reference value $W_1$, respectively; in addition, an instantaneous amplitude of the excitation current $i_{exc}$ may be used to generate the amplitude control signal $y_{AM}$. Such amplitude control circuits are familiar to those skilled in the art. As an example of such an amplitude control circuit, reference is again made to Coriolis mass flowmeters of the "PROMASS I" series. Their amplitude control circuit is preferably designed so that the lateral vibrations of flow tube 13 are maintained at a constant amplitude, i.e., at an amplitude which is also independent of the density $\rho$.

The frequency control signal $y_{FM}$ may be provided by a suitable frequency control circuit 52 which updates this signal based, for example, on at least the sensor signal $s_1$ and on a DC voltage that is representative of the frequency to be adjusted and serves as a frequency reference value $W_2$.

Preferably, frequency control circuit 52 and driver circuit 53 are interconnected to form a phase-locked loop which is used in the manner familiar to those skilled in the art to keep the frequency control signal $y_{FM}$ in phase with an instantaneous resonance frequency of flow tube 13 based on a phase difference measured between at least one of the sensor signals $s_1$, $s_2$ and the excitation current to be adjusted or the measured excitation current, $i_{exc}$. The configuration and use of such phase-locked loops for driving flow tubes at one of their mechanical resonance frequencies are described in detail U.S. Pat. No. 4,801,897, for example. Of course, it is also possible to use other frequency control loops familiar to those skilled in the art, such as those described in U.S. Pat. Nos. 4,524,610 or 4,801,897, for example. Furthermore, regarding the use of such frequency control loops for transducers of the kind being described, reference is made to the aforementioned "PROMASS I" series.

In a further preferred embodiment of the invention, the amplitude control circuit 51 and the frequency control circuit 52 are implemented by means of a digital signal processor DSP and by means of program codes running therein. The program codes may, for instance, be stored in a nonvolatile memory EEPROM of a microcomputer 55 controlling and/or monitoring the signal processor DSP, and be loaded upon start-up of signal processor DSP into a volatile data memory RAM of meter electronics 50, which is incorporated in signal processor DSP, for example. Signal processors suitable for such applications are, for example, those of the type TMS320VC33, which are marketed by Texas Instruments Inc.

It goes without saying that for the processing in signal processor DSP, the sensor signal $s_1$ and, if present, the sensor signal $s_2$ have to be converted to corresponding digital signals by means of suitable analog-to-digital converters A/D; see particularly EP-A 866 319. If necessary, control signals provided by the signal processor, such as the amplitude control signal $y_{AM}$ or the frequency control signal $y_{FM}$, have to be converted from digital to analog form in a corresponding manner.

Since, as repeatedly indicated, such vibratory transducer assemblies, besides inducing fluid friction forces, also induce mass-flow-rate-dependent Coriolis forces and fluid-density-dependent mass inertial forces, for example, according to a preferred development of the invention, the viscometer serves to determine not only the viscosity, $\eta$, but also a density, $\rho$, and a mass flow rate, $\dot{m}$, of the fluid, particularly simultaneously, and to provide a corresponding measured density value $X_\rho$ and a measured mass flow rate value $X_{\dot{m}}$. This may be done using the methods employed to measure mass flow rate and/or density in conventional Coriolis mass flowmeter-densimeters, particularly in those of the aforementioned "PROMASS I" series, which methods are familiar to those skilled in the art; cf. U.S. Pat. Nos. 4,187,721, 4,876,879, 5,648,616, 5,687,100, 5,796,011, or 6,073,495.

To generate the measured viscosity value $X_\eta$, meter electronics 50 derive from the excitation power $P_{exc}$ fed into excitation assembly 16, which power serves in particular to compensate the internal friction produced in the fluid in the manner described above, a first intermediate value $X_1$, particularly a digital value, which represents the vibration-damping friction forces in the fluid; in addition to or instead of the actually injected excitation power $P_{exc}$, an excitation power predetermined by meter electronics 50 and represented, for example, by the amplitude control signal $y_{AM}$ and/or the frequency control signal $y_{FM}$ supplied to driver circuit 50, may serve to determine the viscosity value $X_\eta$ and particularly the intermediate value $X_1$.

In a preferred embodiment of the invention, the intermediate value $X_1$ is determined by means of the excitation current predetermined by meter electronics 50 and/or by means of the actually injected, measured excitation current $i_{exc}$, particularly by means of the amplitude or a moving average of this excitation current. In that case, the excitation current $i_{exc}$ serves as a measure of the entirety of the damping forces counteracting the deflection motions of the vibrating flow tube 13. When using the excitation current $i_{exc}$ to determine the intermediate value $X_1$, however, the fact that the aforementioned damping forces are also dependent, on the one hand, on the viscosity-dependent frictions within the fluid and, on the other hand, on mechanical frictions in excitation assembly 16 and in the vibrating flow tube, for example, has to be taken into account.

To separate the information about the viscosity of the fluid from the excitation current $i_{exc}$, the latter is therefore reduced in meter electronics 50 by the value of a no-load current that is virtually independent of the fluid friction, this no-load current being measured with flow tube 13 evacuated or at least not filled with liquid. The usually long-term-stable no-load current can be readily determined in advance during a calibration of the viscometer, for example, and stored in meter electronics 50, e.g., in the nonvolatile memory EEPROM, in the form of a digital value.

Preferably, the intermediate value $X_1$ is also formed by simply determining a numeric difference between one or more digital excitation current values, representing, for example, the instantaneous amplitude or an instantaneous average value of the excitation current $i_{exc}$, and the digital no-load current value. If the excitation current value represents the amplitude or the average value of the excitation current $i_{exc}$, an amplitude or a corresponding average value of the no-load current must, of course, be subtracted therefrom to obtain the intermediate value $X_1$. The excitation current value can be obtained, for example, by a simple current measurement at the output of driver circuit 53. Preferably, however, the excitation current value, and thus the intermediate value $X_1$, is determined indirectly using the amplitude control signal $y_{AM}$ provided by amplitude control circuit 51, as shown schematically in FIG. 2. This has the advantage of eliminating the need for additional current measurement and particularly for measuring circuits necessary therefor.

Taking into account the relationship $$\sqrt{\eta} \sim i_{exc} \quad (1)$$

which is described in U.S. Pat. No. 4,524,610 and according to which the excitation current $i_{exc}$, at least at a constant density $\rho$, is very well correlated with the square root of the viscosity, $\eta$, in order to determine of the viscosity value $X_\eta$, first the square of the intermediate value $X_1$ derived from the excitation current $i_{exc}$ is formed within meter electronics 50.

It turned out that, if the viscosity value $X_\eta$ is determined only by means of the intermediate value $X_1$, it may be much too inaccurate for many industrial applications in spite of the viscosity and density remaining virtually constant.

Investigations of the phenomenon under laboratory conditions, i.e., using fluids of known, particularly constant, viscosity and density, have shown that the intermediate value $X_1$ is highly responsive not only to trapped gas bubbles but above all to inhomogeneities in the moving fluid. Such inhomogeneities may be air bubbles introduced into the fluid or particles of solid matter entrained with the fluid. Even slight disturbances of the homogeneity in the moving fluid may lead to considerable errors in the measured viscosity value $X_\eta$ which are of the order of up to one hundred times the actual viscosity, $\eta$, of the fluid.

By evaluating a number of waveforms of the excitation current $i_{exc}$ which were recorded during measurements performed in different liquids that were disturbed in a predetermined manner, the inventors found to their surprise that, on the one hand, the excitation current $i_{exc}$ may vary considerably over time despite essentially unchanged conditions, e.g., in the case of a steadily flowing liquid of constant density and viscosity and with an essentially constant content of entrained air bubbles. On the other hand, however, it was ascertained that the excitation current $i_{exc}$, which varies in a virtually unpredeterminable manner, particularly its amplitude, and thus the intermediate value $X_1$, exhibits an empiric standard deviation $s_{iexc}$ or an empiric variance which is very closely correlated with the degree of inhomogeneity.

According to the invention, meter electronics 50 derive from this a second internal intermediate value $X_2$, which, serving to assess the influence of inhomogeneities in the fluid, which was not taken into account in the formation of the intermediate value $X_1$, is used in the determination of the viscosity value $X_\eta$ to weight the intermediate value $X_1$.

The use of the intermediate value $X_2$ is based on recognition that, on the one hand, the intermediate value $X_1$ alone can provide sufficiently accurate information about the viscosity, $\eta$, of the fluid only if the fluid is largely homogeneous, and that, on the other hand, as described above, the instantaneous inhomogeneities in the fluid can be assessed very accurately and largely independently of the fluid based on the waveform of the injected excitation current $i_{exc}$.

In a further preferred embodiment of the invention, to obtain the viscosity value $X_\eta$, the intermediate value $X_1$ is normalized to the intermediate value $X_2$ by a simple numerical division, so that the viscosity value $X_\eta$ is $$X_\eta = \frac{K_1}{X_\rho} \cdot \left(\frac{X_1}{X_2}\right)^2 \quad (2)$$

where $K_1$=a device constant, dependent in particular on the geometry of flow tube 13.

The density value $X_\rho$ in the denominator of Eq. (2) only takes account of the fact that actually the square of the current provides the information about the product of density and viscosity, see also U.S. Pat. No. 4,524,610.

Figure 6:
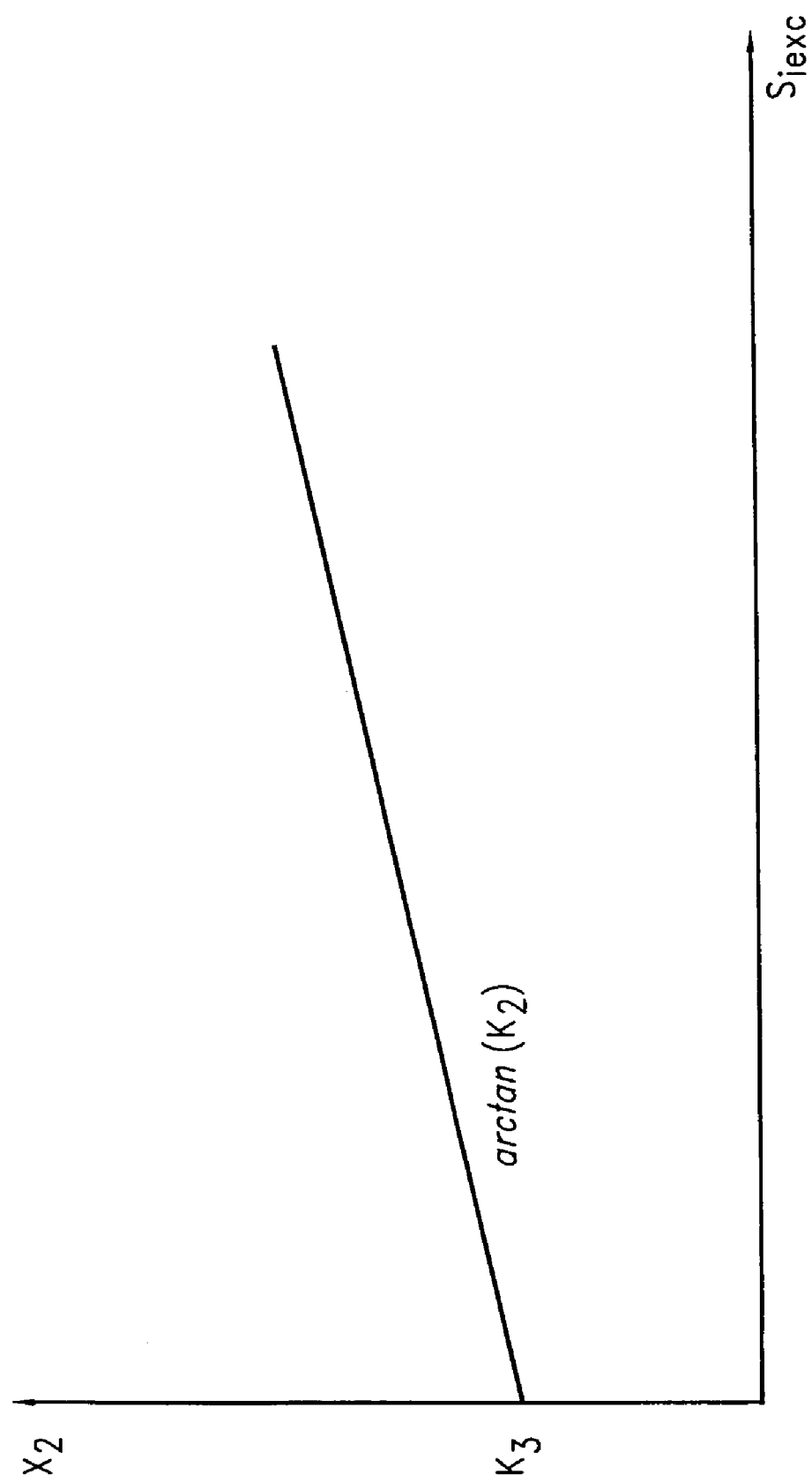
FIG. 6 is a diagram symbolizing steps implemented in the meter electronics for the determination of the viscosity value.

Furthermore, it turned out to the inventors' surprise, that in determining the viscosity value according to Eq. (2), the internal intermediate value $X_2$ can be easily determined according to the linear relationship $$X_2 = K_2 \cdot S_{iexc} + K_3 \quad (3)$$

where $K_2, K_3$=constants determined by calibration which, as is readily apparent, correspond to the slope and offset, respectively, of a simple equation of a straight line, cf. FIG. 6.

To determine the two constants $K_2, K_3$, during a calibration for two calibration fluids of known and, if possible, constant viscosity and of inhomogeneities which differ but remain unchanged, both the instantaneous standard deviation is estimated for the respective excitation current, particularly for its amplitudes, and a ratio $X_\eta/\eta$ of the respective measured viscosity value to the respective instantaneous viscosity is formed. The first calibration fluid (subscript I) may be flowing water with air bubbles introduced therein, for example, and for the second calibration fluid (subscript II), water may be used which is as homogeneous as possible.

For the above-described case where the viscosity is to be determined according to Eq. (2), the two constants $K_2, K_3$ can be calculated from $$K_2 = \frac{\sqrt{\frac{X_{\eta,I}}{\eta_I}} - \sqrt{\frac{X_{\eta,II}}{\eta_{II}}}}{S_{iexc,I} - S_{iexc,II}} \quad (4)$$

$$K_3 = \sqrt{\frac{X_{\eta,I}}{\eta_I}} - K_2 \cdot S_{iexc,I}$$

The respective empiric standard deviation $S_{iexc}$ is preferably calculated by means of a sampling AF of intermediate values $X_1$, stored in digital form in volatile data memory RAM, for example, according to the known function $$s_{iexc} = \sqrt{\left[\frac{1}{m-1} \sum_{j=1}^{m} \left(X_{1,j} - \frac{1}{m}\sum_{j=1}^{m} X_{1,j}\right)^2\right]} \quad (5)$$

If necessary, the sampling AF serving to determine the standard deviation may also be a correspondingly stored sampling sequence of an amplitude characteristic of the excitation current $i_{exc}$, i.e., a section of a digitized envelope of the excitation current $i_{exc}$.

Investigations have shown that for a sufficiently accurate estimate of the standard deviation $S_{iexc}$, samplings of relatively small size m, e.g., approximately 100 to 1000 intermediate values $X_1$, are necessary, with the individual intermediate values $X_1$ having to be sampled only within a very narrow window of about 1 to 2 seconds. Accordingly, a relatively low sampling frequency on the order of few kilohertz, e.g., about 1 to 5 kHz, would be sufficient.

The intermediate value $X_2$ can advantageously also be used to signal the degree of inhomogeneity of the fluid, or measured values derived therefrom, such as a percentage of air contained in the fluid or a content by volume or mass of particles of solid matter entrained with the fluid, e.g., on site or in a remote control room in a visually perceptible manner.

The viscosity value $X_\eta$ determined according to Eq. (2) represents a good estimate of a dynamic viscosity of the fluid, which, as is well known, may also be obtained as the product of the kinematic viscosity and the density $\rho$ of the fluid. If the viscosity value $X_\eta$ is to serve as an estimate of the kinematic viscosity, a suitable normalization to the density value $X_\rho$ must be performed prior to its output, e.g., by a simple numerical division. To that end, Eq. (2) may be modified as follows:

$$X_\eta = K_1 \cdot \left(\frac{X_1}{X_\rho \cdot X_2}\right)^2 \quad (6)$$

It also turned out that for such viscometers with such a flexural mode transducer, particularly if the vibration amplitude is maintained at a constant value, a ratio $i_{exc}/\theta$ of the excitation current $1_{exc}$ to a velocity $\theta$ of a motion causing the internal frictions and, thus, the friction forces in the fluid, which velocity is not measurable directly, is a more accurate estimate of the above-mentioned damping that counteracts the deflections of flow tube 13.

Therefore, in order to further increase the accuracy of the viscosity value $X_\eta$, particularly to reduce its sensitivity to varying vibration amplitudes of flow tube 13, in another preferred embodiment of the invention, the intermediate value $X_1$ is first normalized to a velocity value $X_\theta$, which represents the above-mentioned velocity $\theta$. Put another way, a normalized intermediate value $X_1^*$ is formed according to the following rule:

$$X_1^* = \frac{X_1}{X_\theta} \quad (7)$$

Based on recognition that, particularly if a flexural mode transducer assembly is used for transducer 10, the motion causing the internal friction in the fluid very closely correlates with the motion of the vibrating flow tube 13, which is detected by means of sensor 17 or by means of sensors 17 and 18, the velocity value $X_\theta$ is preferably derived by means of meter electronics 50, e.g., by means of an internal amplitude-measuring circuit 55, from the at least one sensor signal $s_1$, which has already been digitized if necessary. The use of the at least one sensor signal s, not only has the advantage that, as mentioned above, practically no basic changes are necessary in the mechanical design of the transducer assemblies of conventional Coriolis mass flowmeters, but that it is also possible to use the respective sensor arrangements of such transducer assemblies virtually unchanged.

Using the normalized intermediate value $X_1^*$, the viscosity value may then be determined from $$X_\eta = \frac{K_1}{K_f \cdot X_\rho} \cdot \left(\frac{X_1^*}{X_2}\right)^2 \quad (8)$$

The correction factor $K_f$ introduced in Eq. (8) serves to weight the density value $X_\rho$ with the instantaneous vibration frequency of the vibrating flow tube 13.

At this point it should be pointed out once again that the sensor signal $s_1$ is preferably proportional to a velocity of a, particularly lateral, deflection motion of the vibrating flow tube 13; the sensor signal $s_1$ may also be proportional to an acceleration acting on the vibrating flow tube 13 or to a displacement of the vibrating flow tube 13. If the sensor signal $s_1$ is proportional to a velocity in the above sense, the correction factor $K_f$ will correspond to the vibration frequency of the vibrating flow tube 13, while in the case of a sensor signal $s_1$ proportional to a displacement, the correction factor $K_f$ will be equal to the cube of the vibration frequency.

The aforementioned functions serving to generate the viscosity value $X_\eta$, which are symbolized by Eqs. (1) to (8), are implemented at least in part in an evaluation stage 54 of meter electronics 50, which is advantageously realized by means of signal processor DSP, as shown, or by means of microcomputer 55, for example.

The creation and implementation of suitable algorithms corresponding with the above-described functions or simulating the operation of amplitude control circuit 51 or frequency control circuit 52, and their translation into program codes executable in such signal processors, is familiar to those skilled in the art and, therefore, does not require detailed explanation. Of course, the aforementioned equations may also be represented, in whole or in part, by means of suitable analog and/or digital discrete computing circuits in meter electronics 50.

The viscometer according to the invention has an added advantage in that the viscosity value provided by it, $X_\eta$, because of its insensitivity to inhomogeneities in the fluid, also exhibits low cross sensitivity to changes in mass flow rate or density.

The invention claimed is:

1. A viscometer for a fluid flowing in a pipe, said viscometer comprising:
    a vibratory transducer, with at least one flow tube for conducting the fluid and for generating friction forces acting in the fluid, said at least one flow tube communicating with the pipe and vibrating in operation, and with an excitation assembly for vibrating said at least one flow tube; and
    meter electronics which deliver an excitation current ($I_{exc.}$) for said excitation assembly, and a viscosity value ($X_\eta$) representing the instantaneous viscosity of the fluid, said meter electronics generating a first internal intermediate value ($X_1$), corresponding with the excitation current ($i_{exc.}$) and representing the friction forces acting in the fluid, and a second internal intermediate value ($X_2$), representing in homogeneities in the fluid, said meter electronics determining the viscosity value using the first and second internal values ($X_1$, $X_2$).

2. A viscometer as set forth in claim 1, wherein:
    said vibratory transducer comprises a sensor arrangement for sensing vibrations of said at least one flow tube and for generating at least a first sensor signal ($S_1$) representing said vibrations.

3. A viscometer as set forth in claim 2, wherein:
    said meter electronics adjust the excitation current ($i_{exc.}$) by means of said at least first sensor signal ($S_1$).

4. A viscometer as set forth in claim 2, wherein:
said meter electronics determine the first internal intermediate value ($X_1$) by means of an amplitude control signal ($Y_{AM}$) serving to adjust the excitation current ($i_{exc}$).

5. A viscometer as set forth in claim 2 wherein:
to generate said viscosity value ($X_\eta$) said meter electronics determine by means of said at least first sensor signal ($S_1$) a velocity value ($X_\Theta$) which represents motions causing the friction forces in the fluid.

6. A viscometer as set forth in claim 1 wherein:
to produce friction forces acting in the fluid, said at least one flow tube vibrates at least in part in a flexural mode.

7. A viscometer as set forth in claim 1 wherein:
said meter electronics determines said second internal intermediate value ($X_2$) by means of said excitation current ($i_{exc}$).

8. A viscometer for a fluid flowing in a pipe, said viscometer comprising:
a transducer, particularly a flexural mode transducer, with at least one flow tube for conducting the fluid and for producing friction forces acting in the fluid, said at least one flow tube communicating with the pipe and vibrating in operation, with an excitation assembly for vibrating said at least one flow tube, and with a sensor arrangement for sensing vibrations of said at least one flow tube and for generating at least a first sensor signal representing said vibrations; and
meter electronics, which delivers an excitation current ($i_{exc}$) for said excitation assembly and a viscosity value ($X_\eta$) representing the instantaneous viscosity of the fluid, which derives from said at least first sensor signal ($S_1$) an amplitude control signal ($Y_{am}$) serving to adjust said excitation current ($i_{exc}$), and which determines said viscosity value ($X_\eta$) by means of said at least first sensor signal ($S_1$) and said amplitude control signal ($Y_{am}$).

9. A viscometer as set forth in claim 8 wherein:
to generate said viscosity value ($X_\eta$), said meter electronics determine a first internal intermediate value ($X_1$), corresponding with said excitation current ($i_{exc}$) and representing the friction forces acting in the fluid, by means of said amplitude control signal ($Y_{AM}$).

10. A viscometer as set forth in claim 9 wherein:
to generate said viscosity value ($X_\eta$), said meter electronics normalize said first internal intermediate value ($X_1$) to said velocity value ($X_\Theta$).

11. A viscometer as set forth in claim 9 wherein:
said meter electronics generates a second internal intermediate value ($X_2$), representing inhomogeneities in the fluid, and
determines said viscosity value ($X_\eta$) using said first and second internal
intermediate values ($X_1$, $X_2$).

* * * * *